United States Patent [19]

Brake et al.

[11] Patent Number: 4,752,576
[45] Date of Patent: Jun. 21, 1988

[54] EXPRESSION OF α-1 ANTITRYPSIN IN YEAST

[75] Inventors: Anthony J. Brake, Berkeley; Robert A. Hallewell, San Francisco; Steven Rosenberg, Oakland, all of Calif.

[73] Assignee: Chiron Corporation, Emeryville, Calif.

[21] Appl. No.: 620,662

[22] Filed: Jun. 14, 1984

[51] Int. Cl.$^4$ .................... C12P 21/00; C12P 21/02; C12N 1/16; C12N 1/00
[52] U.S. Cl. ..................... 435/68; 435/255; 435/320; 435/70; 935/37; 935/60; 935/69; 935/97
[58] Field of Search ............... 435/68, 70, 172.3, 255, 435/317, 941; 935/37, 60, 69, 97

[56] References Cited

U.S. PATENT DOCUMENTS 4,599,311  7/1986  Kawasaki ........................ 435/68

OTHER PUBLICATIONS

Guarente, L. et al, "A Galio-CYCl Hybrid Yeast Promoter...", *Proc. Natl. Acad. Sci. USA* 79: 7410–7414, 1982.
Zhu, X-L et al, "Control of Herpes Simplex Virus...", *Mol. Gen. Genet.* 194: 31–41, 1984.
Kosikov, K. V. et al, *Biological Abstracts* 66(4):20961, 1977.
Cai, J. et al, *Biological Abstracts* 75(11):79940, 1982.
Courtney et al., Proc. Natl. Acad. Sci. USA (1984), 81:699–673.
Kawasaki et al., "The Production of Human Alpha-1 Antitrypsin in Yeast", in the Molecular Biology of Yeast, p. 230 (Cold Spring Harbor Laboratory 1983).
Russell et al., "Expression of Human Alpha-1 Antitrypsin in Fission Yeast", ibid, p. 231.
Carrell et al., *Nature* (1982), 298329–334.
Kurachi et al., *Proc. Natl. Acad. Sci. USA* (1981), 78:6826–6830.
Bollen et al., *DNA* (1983), 2:255–264.

*Primary Examiner*—Thomas G. Wiseman
*Assistant Examiner*—Robin Lyn Teskin
*Attorney, Agent, or Firm*—Ciotti & Murashige, Irell & Manella

[57] ABSTRACT

Methods and compositions are provided for high level production of foreign proteins in yeast. The system is exemplified by production of $\alpha_1$-antitrypsin in yeast strain AB110, derived from yeast strains 2150-2-3 and AB103.1.

*S. carlsbergensis/S. cerevisiae* hybrid strain AB110 containing plasmid pCl/1GAPATi9 was deposited at the A.T.C.C. on May 9, 1984, and given Accession No. 20709.

18 Claims, 1 Drawing Sheet

FIG. 1

```
                                                                              -24
                                                                      Met Pro Ser Ser
                                           GGGGGGGGGGAGGGTAATCGACA ATG CCG TCT TCT
      -20                                    -10                                    -1
      Val Ser Trp Gly Ile Leu Leu Leu Ala Gly Leu Cys Cys Leu Val Pro Val Ser Leu Ala
      GTC TCG TGG GGC ATC CTC CTG CTG GCA GGC CTG TGC TGC CTG GTC CCT GTC TCC CTG GCT

1 Glu Asp Pro Gln Gly Asp Ala Ala Gln Lys Thr Asp Thr Ser His His Asp Gln Asp His
    1 GAG GAT CCC CAG GGA GAT GCT GCC CAG AAG ACA GAT ACA TCC CAC CAT GAT CAG GAT CAC
          - --- -- BamHI

21 Pro Thr Phe Asn Lys Ile Thr Pro Asn Leu Ala Glu Phe Ala Phe Ser Leu Tyr Arg Gln
   61 CCA ACC TTC AAC AAG ATC ACC CCC AAC CTG GCT GAG TTC GCC TTC AGC CTA TAC CGC CAG

41 Leu Ala His Gln Ser Asn Ser Thr Asn Ile Phe Phe Ser Pro Val Ser Ile Ala Thr Ala
  121 CTG GCA CAC CAG TCC AAC AGC ACC AAT ATC TTC TTC TCC CCA GTG AGC ATC GCT ACA GCC

61 Phe Ala Met Leu Ser Leu Gly Thr Lys Ala Asp Thr His Asp Glu Ile Leu Glu Gly Leu
  181 TTT GCA ATG CTC TCC CTG GGG ACC AAG GCT GAC ACT CAC GAT GAA ATC CTG GAG GGC CTG

81 Asn Phe Asn Leu Thr Glu Ile Pro Glu Ala Gln Ile His Glu Gly Phe Gln Glu Leu Leu
  241 AAT TTC AAC CTC ACG GAG ATT CCG GAG GCT CAG ATC CAT GAA GGC TTC CAG GAA CTC CTC

Arg(a,c)                                                        Asp Gly(c)
  101 His Thr Leu Asn Gln Pro Asp Ser Gln Leu Gln Leu Thr Thr Gly Asn Gly Leu Phe Leu
  301 CAT ACC CTC AAC CAG CCA GAC AGC CAG CTC CAG CTG ACC ACC GGC AAT GGC CTG TTC CTC

121 Ser Glu Gly Leu Lys Leu Val Asp Lys Phe Leu Glu Asp Val Lys Lys Leu Tyr His Ser
  361 AGC GAG GGC CTG AAG CTA GTG GAT AAG TTT TTG GAG GAT GTT AAA AAG TTG TAC CAC TCA

141 Glu Ala Phe Thr Val Asn Phe Gly Asp Thr Glu Glu Ala Lys Lys Gln Ile Asn Asp Tyr
  421 GAA GCC TTC ACT GTC AAC TTC GGG GAC ACC GAA GAG GCC AAG AAA CAG ATC AAC GAT TAC

161 Val Glu Lys Gly Thr Gln Gly Lys Ile Val Asp Leu Val Lys Glu Leu Asp Arg Asp Thr
  481 GTG GAG AAG GGT ACT CAA GGG AAA ATT GTG GAT TTG GTC AAG GAG CTT GAC AGA GAC ACA

181 Val Phe Ala Leu Val Asn Tyr Ile Phe Phe Lys Gly Lys Trp Glu Arg Pro Phe Glu Val
  541 GTT TTT GCT CTG GTG AAT TAC ATC TTC TTT AAA GGC AAA TGG GAG AGA CCC TTT GAA GTC

Ala(b)
  201 Lys Asp Thr Glu Glu Glu Asp Phe His Val Asp Gln Val Thr Thr Val Lys Val Pro Met
  601 AAG GAC ACC GAG GAA GAG GAC TTC CAC GTG GAC CAG GTG ACC ACC GTG AAG GTG CCT ATG
                                                          - --- --- BstEII

221 Met Lys Arg Leu Gly Met Phe Asn Ile Gln His Cys Lys Lys Leu Ser Ser Trp Val Leu
  661 ATG AAG CGT TTA GGC ATG TTT AAC ATC CAG CAC TGT AAG AAG CTG TCC AGC TGG GTG CTG

Asn(c)
  241 Leu Met Lys Tyr Leu Gly Asn Ala Thr Ala Ile Phe Phe Leu Pro Asp Glu Gly Lys Leu
  721 CTG ATG AAA TAC CTG GGC AAT GCC ACC GCC ATC TTC TTC CTG CCT GAT GAG GGG AAA CTA

261 Gln His Leu Glu Asn Glu Leu Thr His Asp Ile Ile Thr Lys Phe Leu Glu Asn Glu Asp
  781 CAG CAC CTG GAA AAT GAA CTC ACC CAC GAT ATC ATC ACC AAG TTC CTG GAA AAT GAA GAC
                                        --- --- EcoRV

281 Arg Arg Ser Ala Ser Leu His Leu Pro Lys Leu Ser Ile Thr Gly Thr Tyr Asp Leu Lys
  841 AGA AGG TCT GCC AGC TTA CAT TTA CCC AAA CTG TCC ATT ACT GGA ACC TAT GAT CTG AAG

Val(a,c)
  301 Ser Ile Leu Gly Gln Leu Gly Ile Thr Lys Val Phe Ser Asn Gly Ala Asp Leu Ser Gly
  901 AGC ATC CTG GGT CAA CTG GGC ATC ACT AAG GTC TTC AGC AAT GGG GCT GAC CTC TCC GGG

321 Val Thr Glu Glu Ala Pro Leu Lys Leu Ser Lys Ala Val His Lys Ala Val Leu Thr Ile
  961 GTC ACA GAG GAG GCA CCC CTG AAG CTC TCC AAG GGC GTG CAT AAG GCT GTG CTG ACC ATC

341 Asp Glu Lys Gly Thr Glu Ala Ala Gly Ala Met Phe Leu Glu Ala Ile Pro Met Ser Ile
 1021 GAC GAG AAA GGG ACT GAA GCT GCT GGG GCC ATG TTT TTA GAG GCC ATA CCC ATG TCT ATC

361 Pro Pro Glu Val Lys Phe Asn Lys Pro Phe Val Phe Leu Met Ile Glu Gln Asn Thr Lys
 1081 CCC CCC GAG GTC AAG TTC AAC AAA CCC TTT GTC TTC TTA ATG ATT GAA CAA AAT ACC AAG
              --- --- AvaI

381 Ser Pro Leu Phe Met Gly Lys Val Val Asn Pro Thr Gln Lys OC
 1141 TCT CCC CTC TTC ATG GGA AAA GTG GTG AAT CCC ACC CAA AAA TAA CTGCCTCTCGCTCCTCAAC
                                              - --- - HinfI AAT CCC ACC CAA AAA TAG
                                          GGG TGG GTT TTT ATC AGCT
                                                            - ---- SalI 1201 CCCTCCCCTCCATCCCTGGCCCCCTCCCTGGATGACATTAAAGAAGGGTTGAGCTGGAAAAAAAAAAAAAAAAAAAAA
```

EXPRESSION OF α-1 ANTITRYPSIN IN YEAST

BACKGROUND OF THE INVENTION

1. Field of the Invention

Hybrid DNA technology provides the opportunity to produce any amino acid sequence from naturally occurring amino acids. However, to use this ability in a useful manner has involved the overcoming of numerous obstacles, many of them associated with unknown factors involved with replication and expression in unicellular microorganism hosts. While the basic concepts of transcription of DNA to messenger RNA, splicing, and translation have seen enormous expansions in understanding of the processes involved, nevertheless the stability of messenger RNA, the rapidity with which it is translated, the stability of foreign proteins in the microorganisms, and the efficiency of processing and secretion, are still understood only at a rudimentary level.

For many polypeptides, the economies of manufacture will determine their utility. It will therefore be important that systems be developed, where the vectors, markers, regulatory signals, and host cooperate to provide for the production of the desired polypeptide in a form and at a level of total protein in which it may be readily isolated and purified. Desirably, where the natural product is processed to a mature protein, the host may afford partial or complete processing.

It is thus of vital importance to the development of useful proteins for industrial and therapeutic purposes to efficiently produce in high yields polypeptides of interest employing systems which can be readily developed, can be stably maintained and employ a host which can be grown in industrially efficient ways.

2. Description of the Prior Art

Carrell et al., Nature (1982) 298: 329-334 provide the amino acid sequence of human $\alpha_1$-antitrypsin, with discussion of various known antitrypsin mutants. Kurachi et al., Proc. Natl. Acad. Sci. USA (1981) 78: 6826-6830 present the entire cDNA sequence of baboon $\alpha_1$-antitrypsin. A partial human cDNA clone sequence is also shown. Bollen et al., DNA (1983) 2: 255-264 describe the cloning and expression in E. coli of a full cDNA coding for human $\alpha_1$-antitrypsin. Courtney et al., Proc. Natl. Acad. Sci. USA (1984) 81: 669-673 describe the expression of human cDNA for $\alpha_1$-antitrypsin in E. coli. Kawasaki et al., "The Production of Human $\alpha_1$-antitrypsin in Yeast and Fission Yeast" in The Molecular Biology of Yeast, Cold Spring Harbor Laboratory, 1983, describe the expression of human $\alpha_1$-antitrypsin in S. cerevisiae and S. pombe employing the yeast triosephosphate isomerase promoter and terminator sequences. The protein is reported to be unglycosylated, but biologically active against trypsin and elastase.

SUMMARY OF THE INVENTION

Methods, compositions and yeast systems are provided for expression of heterologous proteins in high yield in yeast. Particularly, yeast DNA sequences associated with transcriptional and translational control of glycolytic enzymes are employed in conjunction with structural genes encoding proteins foreign to yeast, where the construction is employed in a yeast host providing for high yield of the expression product. Particularly, human $\alpha_1$-antitrypsin is produced in excess of 5% of total soluble protein.

DESCRIPTION OF THE FIGURE

FIG. 1 shows the nucleotide and predicted amino acid sequences of alpha-antitrypsin.

DESCRIPTION OF THE SPECIFIC EMBODIMENTS

Novel yeast systems are provided for the enhanced production of proteins foreign to yeast. The system involves the selection of a yeast host obtained by crossing different strains of Saccharomyces having the desired genotype, wherein one of the strains contains an expression plasmid which includes a structural gene of interest. The expression plasmid has an efficient transcriptional initiation system for transcriptional regulation of the structural gene. The resulting crosses are selected for enhanced production of the polypeptide of interest. In this manner, novel strains are produced which are specifically adapted to the efficient and enhanced expression of a desired foreign protein.

Of particular interest as the host is a cross between two strains, employing the common fermenting strain S. carlsbergensis having the appropriate auxotrophy, which may be a laboratory or industrial strain, mated with an S. cerevisiae strain having the appropriate genotype, so as to provide for a strain which can be selected having the desired properties. The two strains will usually have at least one common genetic lesion, so that the progeny will also have the same lesion. Particularly, the resulting strain should be pep⁻ particularly pep4⁻ and auxotrophic in a convenient metabolite, which can be complemented with an extrachromosomal marker, for example a cross between two different Saccharomyces strains, the carlsbergensis leu⁻ strain 2150-2-3 (available from Lee Hartwell, University of Washington) and the cerevisiae leu⁻ strain AB103.1 (ATCC Accession No. 20711), where one of the cell lines, particularly the AB103.1 cell line bears the pep4⁻ mutation and carries the expression plasmid. A strain was selected, "cured" of the plasmid and designated AB110, which has the following genotype: MAT α, ura3-52, leu2-04 or both leu2-3 and leu2-112, pep4-3, his4-580 [cir°].

The host is used with an expression vector, which includes an efficient promoter system. Particularly, the promoter regions from yeast glycolytic enzyme genes are employed, where fewer than 600 bp, usually from about 300 to 550 bp of the promoter region upstream from the initiation codon of the structural gene is employed. This sequence from the promoter region extends downstream to at least about the nucleotide −20, more usually to at least about the nucleotide −10, and generally not beyond the nucleotide +3. (The numbering is based upon the first base of the initiation codon as +1, while the adjacent upstream base is −1 and numbering in opposite directions therefrom accordingly.) The sequence includes the RNA polymerase binding site (the sequence including nucleotides upstream from the transcription initiation site which provides for initiation of formation of messenger RNA), as well as the transcription initiation site, and may also include the capping sequence, and other sequences associated with transcriptional regulation, as well as with translational regulation.

The promoter region of yeast glycolytic enzyme structural genes appears to be divided into two domains, one domain proximal to the structural gene, which involves the binding of the RNA polymerase and initiation of transcription and a second domain contiguous to the first domain and distal to the structural gene, which provides for enhanced efficiency and/or regulation of transcription. However, the presence of this distal region in recombinant constructs is found to reduce the efficiency of transformation, as well as the viability of the host. Therefore, the RNA polymerase binding region employed in the subject expression system will usually involve solely the first domain, with the second domain being substituted with various other sequences.

These sequences may include various sequences involved with the regulation of transcription of structural genes, such as sequences which result in regulation of transcription in response to a carbon source, nutrient, metabolite, ligand, or the like; or responsive to changes in the physical environment, e.g., temperature. That is, sequences where transcription can be induced by a change in the chemical or physical environment of the host. Alternatively, sequences other than the native sequence may be employed to provide for enhanced efficiency of constitutive transcription.

The proximal domain may be obtained from the promoter region providing for transcription of such glycolytic enzyme structural genes as alcohol dehydrogenase, glyceraldehyde-3-phosphate dehydrogenase, pyruvate kinase, triosephosphate isomerase, phosphoglucoisomerase, phosphofructokinase, glucose-6-phosphate dehydrogenase, or the like.

The distal domain when involving regulatory regions will generally be of at least about 100 base pairs and may be 500 bp or more, usually not exceeding about 2 kbp, more usually not exceeding about 1 kbp. These regions may be derived from such regulatory regions as GAL1, PHO5, GAL10, etc., or may be any of a number of temperature-sensitive sequences, which have been extensively described in the literature. Alternatively, prokaryotic sequences of at least 500 bp, preferably at least about 1000 bp, and usually not exceeding 6 kbp, more usually not exceeding about 5 kbp may be employed to enhance efficiency.

A transcriptional-translational termination region will also be employed 3' to the structural gene, which may be associated with the same or different structural gene from the structural gene with which the promoter domain is associated. Conveniently, it may be a transcriptional termination region associated with the same structural gene. The termination region will usually be at least about 300 bp, and may be 500 bp or more and will include the necessary regulatory sequences for transcriptional and translational termination.

Intermediate the transcriptional and translational regulatory initiation and termination sequences will be a structural gene of interest usually including associated translational initiation and termination codons, the gene usually being foreign to the yeast host. Of particular interest will be genes encoding mammalian proteins, proteins of pathogens, such as viruses or unicellular microorganisms, e.g., bacteria and protozoa, or plant proteins. Of particular interest are proteins which function as enzymes, hormones, structural proteins, lymphokines, plasma proteins, enzyme inhibitors, or the like. Illustrative proteins include $\alpha_1$-antitrypsin, which will be used as exemplary of the subject invention, $\alpha$-, $\beta$- or $\gamma$-interferons, interleukin-2, tissue plasminogen activator, blood factors V to XI, and portions and precursors thereof, e.g., Factor VIIIR and Factor VIIIC, growth hormone, epidermal growth factor, insulin, platelet derived growth factor, superoxide dismutase, thrombin, plasmin, albumin, etc.

The expression vector will have a stable replication system, unless integration is desired. Usually, it will be preferable to maintain an independent extrachromosomal element of either high or low copy number, depending upon the particular construction and the effect of the construct on the viability of the host. Conveniently, the 2 $\mu$m plasmid replication system may be employed. Alternatively a combination may be employed of a centromere sequence and an autonomously replicating segment, e.g., CEN3 and ars1 or 3.

In addition to the other functional sequences, one or more genetic markers may be employed for selection and maintenance. These markers may provide for protection from a biocide, e.g., antibiotic, toxin, or heavy metal; provide prototrophy to an auxotrophic host, e.g., the amino acid his, leu, or trp or other metabolite, e.g., ura, etc., gene; immunity; etc. Preferably the host cell phenotype will be caused by a mutation or lesion resulting in a metabolic block, i.e., in auxotrophy, which can then be complemented by the wild-type, functional, plasmid DNA which was introduced.

Frequently, it will be desirable to have a replication system recognized by bacteria, e.g., $E.$ $coli$, included in the construct, so that during construction of the expression plasmid or afterwards, the construct may be cloned in a bacterial host at intermediate and final stages, isolated and purified. There are numerous replication systems described in the literature derived from such plasmids or viruses as ColE1, lambda, R6, or the like.

The various sequences may be isolated and joined in conventional ways. Gene libraries may be employed, either genomic or cDNA libraries, which are searched employing probes which may be obtained in different ways, depending upon the information which is available. Where an amino acid sequence is known, mixtures of probes can be prepared which encode for the particular sequence. Alternatively, where a fragmentary DNA or RNA sequence is known, a probe can be prepared having the particular sequence. These sequences may be used to identify regions associated with the fragment of interest, for example, a yeast glycolytic enzyme structural gene or desired foreign, e.g., human, gene.

Once the fragment(s) containing the gene(s) of interest is(are) identified by means of the probe, the fragment(s), which will usually be substantially larger than the gene and the regulatory regions associated with the gene, may be manipulated in a variety of ways. Particularly, restriction mapping and sequencing may be employed to identify the specific regions concerned with transcriptional and translational regulation and the coding region. As appropriate, various manipulative changes may be made. One or more bases may be modified, or fragments truncated or extended, by using such techniques as primer repair, in vitro mutagenesis, ligating of adapters or linkers, resection, restriction, or the like. These techniques are well established and may be found in the text, Maniatis et al., Molecular Cloning, Cold Spring Harbor Laboratory, Cold Spring Harbor, N.Y., 1982, or other publications.

Frequently, vectors will be available which can be used in preparing the expression plasmid. Cassettes may be prepared, where the transcriptional and translational initiation and termination regions are separated by a relatively short sequence containing one or more unique restriction sites. In this way, the gene may be inserted at the unique restriction site or may be used as a substitution for a segment between two restriction sites. Once the expression plasmid has been prepared, it may be introduced into the host by conventional techniques, such as polyethylene glycol precipitated DNA with spheroplasts, conjugation, transfection or the like. See, for example, Hinnen et al., *Proc. Natl. Acad. Sci. USA* (1978) 75: 1929-1933.

The modified yeast host is then grown in an appropriate nutrient medium to provide for expression of the desired polypeptide. Conventional rich nutrient media may be used or any other medium in which yeast can be satisfactorily grown, lacking the appropriate metabolite(s). For induced expression, the host will be grown to high density under conditions where expression of the polypeptide is not induced and when the desired cell density is achieved, the conditions will be changed to induce expression. For constitutive expression, the host will be grown in a rich medium to ensure the efficient production of the desired polypeptide.

After sufficient time for the polypeptide to be obtained, the cells may be isolated, lysed by any convenient means, e.g., mechanical shearing or detergent, and the polypeptide of interest isolated and purified by conventional techniques, e.g., chromatography, such as affinity chromatography, electrophoresis, density gradient, crystallization, ultrafiltration, or the like. Where the polypeptide is secreted, the cells may be separated from the supernatant and the supernatant treated as described above.

Of particular interest is the use of the glyceraldehyde-3-phosphate dehydrogenase or pyruvate kinase promoter regions having the RNA polymerase binding site and the transcription initiation site. In conjunction with these promoter regions or proximal domains are desirably used for regulated expression, the GAL4 regulator region or the PHO5 regulator region or a temperature sensitive regulator. The terminator region may be derived from any convenient structural gene, particularly the glycolytic enzyme genes, which have been described previously.

By employing the constructions of the subject invention, polypeptides may be produced in amounts usually of at least 1% of total soluble protein, more usually at least 2% of total soluble protein, and frequently at least 5% or higher, where amounts of about 25% or higher of total soluble protein are attainable, the total soluble protein being the sum of total host and expression product soluble protein.

The following examples are offered by way of illustration and not by way of limitation.

EXPERIMENTAL

All DNA manipulations were done according to standard procedures. See Molecular Cloning, T. Maniatis et al., Cold Spring Harbor Lab., 1982. Enzymes used in cloning were obtained either from New England Biolabs or Bethesda Research Laboratories and employed according to the supplier's directions. Yeast were transformed and grown using a variety of media including selective medium (yeast nitrogen base supplemented with amino acids, etc. as appropriate but without leucine; YEPD medium, containing 1% (w/v) yeast extract, 2% (w/v) peptone and 2% (w/v) glucose; and in the case of plating medium contained 2% (w/v) agar and for transformation 3% top agar).

CLONING AND EXPRESSION OF ALPHA-1-ANTITRYPSIN

Isolation of cDNA gene

A cDNA library was made from 10 $\mu$g of polyA+ RNA isolated from part of a human liver. This library was prepared by oligo-dT priming of the first cDNA strand and self-priming of the second cDNA strand. The ds cDNA was size fractionated on a Sepharose CL4B column and those molecules greater than 300 bp isolated. This fraction was treated with nuclease S1 and tailed with dCTP, using terminal transferase. The tailed cDNA was annealed to pBR322 which had been digested with PstI and tailed with dGTP. Transformation of *E. coli* HB101 yielded 60,000 colonies, where greater than 90% of the clones were recombinant.

Two synthetic oligonucleotide probes were used to isolate the alpha-1-antitrypsin ($\alpha_1$-AT) cDNA, the first probe corresponding to amino acid residues 344-350 near the C-terminus of the protein was used to probe 5,000 colonies and the second probe, corresponding to amino acid residues −23 to −17 (+1 being the first nucleotide of the first codon of the mature $\alpha_1$-AT, with the negative numbers being upstream therefrom) of the signal peptide, was used to probe 25,000 colonies. The probe sequences were taken from the partial nucleotide sequence described by Kurachi et al., *Proc. Natl. Acad. Sci. USA* (1981) 78: 6826; Leicht et al., Nature (1982) 297: 655). Approximately 3% of the colonies hybridized to the C-terminal probe and four hybridized to the N-terminal probe. The four N-terminal clones and 12 C-terminal clones were isolated and subjected to restriction analysis. From these, three overlapping clones which cover the entire cDNA were subjected to further study and were used to construct the full-length cDNA clone.

The entire sequence of a composite full-length cDNA derived from the three plasmids is shown in FIG. 1. The reactive center met-ser at positions 358-359 is boxed. The subscripts to the amino acids in parentheses identify differences between the subject protein sequence and those derived from (a) protein sequencing [Carrell et al., 1982], (b) the cDNA of Woo et al. [see Carrell et al., 1982], and (c) the cDNA of Bollen et al., 1983. The synthetic DNA molecules used in the construction of the BamHI to SalI fragment encoding the mature protein are shown as are the cDNA restriction sites used in this construction.

The above sequence was determined using the dideoxy sequencing method of Sanger et al., *Proc. Natl. Acad. Sci. USA* (1977) 74: 5463, in the M13 vectors of Messing et al., *Nucleic Acids Res.* (1981) 9: 309. The differences at the nucleotide and amino acid level from the published cDNA sequences are shown.

Construction of the full length clone for expression of yeast began with three fragments isolated from cDNA clones: (1) a 630 bp BamHI-BstEII fragment; (2) a 450 bp BstEII-AvaI fragment; and (3) an 85 bp AvaI-HinfI fragment. A synthetic adapter was employed having the following sequence:

$$A_2TC_3AC_3A_5TAG$$
$$G_3TG_3T_5ATCAGCT$$

Approximately two pmoles of fragments 1 and 2 were ligated together and after removal of the ligase, digested with BamHI and AvaI. Fragment 3 and the synthetic adapter were ligated and digested with AvaI and SalI and the two resulting fragment mixtures were ligated followed by digestion with BamHI and SalI. Fragments migrating upon electrophoresis in the region of about 1000–1400 bp were isolated and cloned by substitution into BamHI and SalI digested and alkaline phosphatase treated pBR322. The resulting plasmid is referred to as pATi.

Construction of pPGAP

A yeast expression vector was prepared called pPGAP having a polyrestriction site linker between the GAPDH terminator and a truncated GAPDH promoter region. Plasmids pGAP2 and pGAP1 were obtained as follows: A yeast gene library was prepared by inserting fragments obtained after partial digestion of total yeast DNA with restriction endonuclease Sau3A in lambda-phage Charon 28 (Blattner et al., *Science* (1977) 196: 161–169). The phage library was screened with DNA complementary to the yeast GAPDH mRNA and the yeast GAPDH gene GAP49 (Holland and Holland, *J. Biol. Chem.* (1979) 254: 5466–5474) from one of these clones was subcloned as either an about 3.3 kb BamHI fragment in the BamHI site of pBR322 (pGAP-2) or as an about 2.1 kb HindIII fragment in the HindIII site of pBR322 (pGAP-1). After digestion of the plasmid pGAP1 with HinfI, a 500 bp fragment was gel isolated, the fragment resected with Bal31 to remove about 50 bp, ligated with HindIII linkers, followed by digestion with HindIII and the resulting about 450 bp fragment inserted into the HindIII site of pBR322 after treatment of the plasmid with HindIII followed by alkaline phosphatase. The resulting plasmid pGAP128 was digested with HindIII, the fragment made blunt-ended with the Klenow fragment of DNA polymerase I and nucleotide triphosphates and the resulting blunt-ended about 450 bp fragment gel isolated and inserted into the SmaI site of plot5 after SmaI digestion and alkaline phosphatase treatment to provide the plasmid plot5pGAP128. plot5 was prepared by inserting the 40 bp polylinker fragment of the following sequence

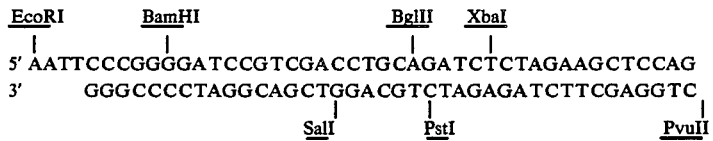

into pBR322 as an EcoRI-PvuII substitution followed by insertion of the trp-lac promoter (Russell and Bennett, *Gene* (1982) 20: 231–245) into the PvuII site with transcription oriented toward the polylinker sequence. Plasmid plot5pGAP128 was then digested with BamHI and TaqI to yield an approximately 390 bp BamHI-TaqI fragment having the −400 to −26 bp of the GAPDH promoter. The BamHI-TaqI fragment was ligated to a synthetic fragment having the following sequence:

and containing −26 to −1 bp of the GAPDH promoter and an NcoI site. The resulting BamHI-SalI fragment, which was digested with BamHI and SalI and used to replace the BamHI-SalI fragment of BamHI-SalI digested pBR322 treated with alkaline phosphatase. After ligation, the plasmid pGAPNRS was obtained which was digested with BamHI and SALI to provide a 400 bp BamHI-SalI fragment which was gel isolated. This fragment was ligated to an about 1 kb SalI-BamHI fragment containing the GAPDH terminator region and a short segment of 3′ coding region and the resulting 1.4 kb BamHI-BamHI fragment digested with BamHI. The about 1 kb SalI-BamHI GAPDH terminator fragment was obtained by gel electrophoresis after SalI and BamHI digestion of pGAP2, prepared as described above.

pBR322 was digested with EcoRI and SalI, the termini blunt-ended and ligated to BamHI linkers, followed by BamHI digestion and the BamHI-BamHI 3.8 kb fragment gel isolated, recircularized by self-ligation, cloned and designated pBRΔR1-Sal. The 1.4 kb BamHI-BamHI fragment was inserted into the BamHI digested, alkaline phosphatase treated pBRΔR1-Sal vector to provide the plasmid pPGAP of about 5.3 kb with the orientation in the opposite direction of the amp$^r$.

Plasmid pPGAP was digested with NcoI, followed by blunt-ending, followed by SalI digestion and treatment with alkaline phosphatase. The NcoI-SalI fragment was substituted with an approximately 1250 bp blunt-ended (BamHI)-SalI fragment obtained from plasmid pATi, by BamHI digestion, blunt ending, and SalI digestion. This was inserted into the pPGAP vector to produce the plasmid pGAPATi, a 6.6 kb plasmid, which was digested with NcoI and BamHI and a 2.3 kb NcoI-BamHI fragment obtained having the $\alpha_1$-AT gene and the GAPDH terminator and approximately 400 bp BamHI-NcoI fragment obtained having the GAPDH promoter. These fragments were ligated together and inserted into the BamHI site of pC1/1. (Plasmid pC1/1 is a derivative of pJDB219 (Beggs, *Nature* (1978) 275: 104) in which the region corresponding to bacterial plasmid pMB9 in pJDB219 has been replaced by pBR322 pC1/1.)

The plasmids pC1/1GAPATi8 and pC1/1GAPATi9 were obtained with the orientation of expression clockwise in the former and counterclockwise in the latter, with amp$^r$ being in the counterclockwise direction. These plasmids were transformed in S. cerevisiae AB103.1 (MATα, pep4-3, leu2-3, leu2-112, ura3-52, his4-580 [cir°]) (A.T.C.C. No. 20711, deposited June 8, 1984) by standard methods (Hinnen et al., *Proc. Natl. Acad. Sci. USA* (1978) 75: 1929–1933), selecting for leucine prototrophy and grown as described above. Yeast extracts were prepared by lysis with glass beads followed by centrifugation at 12,000×g for 10 min and the $\alpha_1$-AT activity determined by inhibition of human leukocyte elastase.

Assays contained in 1 ml: 0.1–0.2 human leukocyte elastase (HLE); 0.1 mM MeO-Suc-Ala-Ala-Pro-Val-p-nitroanilide (Beatty et al., *J. Biol. Chem.* (1980) 255: 3931); 50 mM Tris, pH 8, 0.5M NaCl, and the indicated amounts of yeast extract or human $\alpha_1$-AT. Assays were initiated by the addition of elastase, incubated at 28° C. for 15 min, terminated by the addition of 100 μl of 8N acetic acid and the absorbance at 410 nm determined. Typical results are shown in the following Table 1.

TABLE 1

| Plasmid | Strain | Amt. Extract (μl) | Amt. HLE (μg) | Amt. Protein (μg) | % Elastase Activity | % $\alpha_1$-AT* |
|---|---|---|---|---|---|---|
| pC1/1GAPATi8 | AB103.1 | 5.0 | 0.1 | 50.0 | 40 | 0.17 |
|  |  | 10.0 | 0.1 | 100.0 | 26 | 0.11 |
| pC1/1GAPATi9 | AB103.1 | 0.25 | 0.1 | 2.3 | 89 | 0.7 |
|  |  | 1.0 | 0.1 | 9.1 | 26 | 1.2 |
| pC1/1GAPATi9 | AB110** | 0.2 | 0.2 | 2.9 | 39 | 6.1 |
|  |  | 0.4 | 0.2 | 5.8 | 14 | 4.3 |

*Calculation based upon the Mol. wt. of HLE (29kD), the amount of protein added and the degree of inhibition.
**See below for preparation.

The above data demonstrate that plasmids having the orientation of the expression cassette in the counterclockwise orientation, the promoter proximal to the long sequence of pBR322, make 10–20 times more $\alpha_1$-AT than the same cassette in the other orientation.

Yeast strain AB110

Yeast strain S. carlsbergensis 2150-2-3 (available from Lee Hartwell, University of Washington) was crossed with a yeast S. cerevisiae strain AB103.1 transformant containing pC1/1GAPATi9. The diploids were sporulated and the tetrads dissected. Strains were maintained on leucine selective plates in order to ensure maintenance of the plasmid, since the parents are auxotrophs. A series of colonies were screened for their genotype with respect to a number of markers. The most vigorous strains were selected and cultures grown on leucine selective media. The best strain was designated AB110 (pC1/1GAPATi9), gave 6–7.5% of the total cell protein as $\alpha^1$-AT as shown in the above Table 1. The strain AB110 has the following genotype: MATα, ura3-52, leu2-04 or both leu2-3 and leu2-112, pep4-3, his4-580 [cir°] and is obtained by curing the above strain AB110(pC1/1GAPATi9) of its resident plasmid by growth in the presence of leucine (absence of selective pressure) and then selection for leu⁻ colonies by replica plating.

It is evident from the above results, that by employing a robust brewer's yeast S. carlsbergensis-baker's yeast S. cerevisiae hybrid strain as a host, auxotrophic as to a particular amino acid, for example, leucine, histidine, or tryptophan, and having a pep⁻ mutation particularly in the pep4 gene, greatly enhanced yields of foreign proteins may be obtained. Desirably, after the original mating of the strains, the resulting pep4⁻ strains may be selected and crossed against the parent S. carlsbergensis strain with continuous selection for enhanced yields of the desired product.

Although the foregoing invention has been described in some detail by way of illustration and example for purposes of clarity of understanding, it will be obvious that certain changes and modifications may be practiced within the scope of the appended claims.

What is claimed is:

1. An expression system comprising an S. carlsbergensis/S. cerevisiae hybrid strain which is pep⁻ and has an extrachromosomal element having a marker for selection, a truncated promoter region from a yeast glycolytic enzyme structural gene, wherein said promoter region includes the RNA polymerase binding site and transcription initiation site and is less than about 600 bp, and a gene foreign to yeast under the transcriptional control of said promoter region.

2. A system according to claim 1, wherein said strain is auxotrophic and said marker complements said auxotrophy.

3. A system according to claim 1, wherein said hybrid strain is obtained by mating an S. carlsbergensis strain with an S. cerevisiae strain containing said extrachromosomal element.

4. A system according to claim 1, wherein said hybrid strain is AB110, having A.T.C.C. Accession No. 20709.

5. A system according to claim 4, wherein said foreign gene codes for a mammalian $\alpha_1$-antitrypsin.

6. A system according to claim 1, wherein said foreign gene codes for a mammalian $\alpha_1$-antitrypsin.

7. A system according to claim 1, which is pep4⁻.

8. An expression system comprising an S. carlsbergensis/S. cerevisiae hybrid strain which is pep4⁻, has at least one auxotrophic mutation in at least one gene and has a extrachromosomal element having a gene complementing at least one auxotrophic mutation, a truncated promoter region from a yeast glyceraldehyde-6-phosphate dehydrogenase of less than about 500 bp and extending downstream to at least about nucleotide −20, wherein said promoter region includes the RNA polymerase binding site and transcription initiation site, and a gene foreign to yeast under the transcriptional control of said region.

9. An expression system according to claim 8, wherein upstream from said promoter region and contiguous therewith is a prokaryotic sequence of at least about 500 bp.

10. An expression system according to claim 8, wherein upstream from said promoter region and contiguous therewith is a yeast transcriptional regulatory sequence.

11. An expression system according to claim 10, wherein said regulatory sequence is associated with the regulation of GAL1, GAL10 or PHO5.

12. An expression system according to claim 8, wherein said foreign gene is $\alpha_1$-antitrypsin.

13. A method for producing the expression product of a foreign gene in yeast comprising growing the expression system according to claim 1 in an appropriate nutrient medium.

14. A method for producing the expression product of a foreign gene in yeast, comprising growing the expression system according to claim 8 in an appropriate nutrient medium.

15. A method according to claim 14, wherein said foreign gene is $\alpha_1$-antitrypsin.

16. An S. carlsbergensis/S. cerevisiae hybrid strain obtained by crossing auxotrophic leu⁻ S. carlsbergensis yeast cells with non-complementary leu⁻ pep4⁻ S. cerevisiae yeast cells and selecting for an auxotrophic leu⁻ S. carlsbergensis/S. cerevisiae hybrid strain having higher levels of expression of a foreign gene relative to said S. cerevisiae cells.

17. A hybrid strain according to claim 19 which strain is AB110, A.T.C.C. Accession No. 20709.

18. A hybrid strain resulting from crossing a hybrid strain according to claim 19 with a leu⁻ S. carlsbergensis strain.

* * * * *